United States Patent
Schulze et al.

(10) Patent No.: US 6,835,195 B2
(45) Date of Patent: Dec. 28, 2004

(54) SURGICAL DEVICE FOR APPLYING RADIO FREQUENCY ENERGY TO A PORTION OF A CAPTURED VESSEL

(75) Inventors: Dale R. Schulze, Lebanon, OH (US); Michael F. Clem, Maineville, OH (US); Gary W. Knight, West Chester, OH (US); Christopher J. Hess, Lebanon, OH (US); Rudolph H. Nobis, Mason, OH (US); Gary L. Long, Mariemont, OH (US)

(73) Assignee: Ethicon, Inc., Somerville, NJ (US)

( * ) Notice: Subject to any disclaimer, the term of this patent is extended or adjusted under 35 U.S.C. 154(b) by 79 days.

(21) Appl. No.: 10/318,755

(22) Filed: Dec. 13, 2002

(65) Prior Publication Data

US 2003/0125733 A1 Jul. 3, 2003

Related U.S. Application Data

(62) Division of application No. 09/966,790, filed on Sep. 28, 2001, now Pat. No. 6,572,615.

(51) Int. Cl.$^7$ ............................................... A61B 18/18
(52) U.S. Cl. .......................... 606/50; 606/46; 600/104; 600/105
(58) Field of Search .............................. 600/104–107, 600/114, 170; 606/46–50

(56) References Cited

U.S. PATENT DOCUMENTS

| | | | |
|---|---|---|---|
| 4,430,996 A | * | 2/1984 | Bonnet .................... 606/46 |
| 5,290,286 A | * | 3/1994 | Parins ..................... 606/50 |
| 5,591,183 A | | 1/1997 | Chin |
| 5,593,418 A | | 1/1997 | Mollenauer |
| 5,601,581 A | | 2/1997 | Fogarty et al. |
| 5,667,480 A | | 9/1997 | Knight et al. |
| 5,695,514 A | | 12/1997 | Chin |
| 5,722,934 A | | 3/1998 | Knight et al. |
| 5,725,479 A | | 3/1998 | Knight et al. |
| 5,730,748 A | | 3/1998 | Fogarty et al. |
| 5,797,947 A | | 8/1998 | Mollenauer |
| 5,817,013 A | | 10/1998 | Ginn et al. |
| 5,836,945 A | | 11/1998 | Perkins |
| 5,853,417 A | | 12/1998 | Fogarty et al. |
| RE36,043 E | | 1/1999 | Knighton |
| 5,873,889 A | | 2/1999 | Chin |
| 5,876,413 A | | 3/1999 | Fogarty et al. |
| 5,891,140 A | | 4/1999 | Ginn et al. |
| 5,899,913 A | | 5/1999 | Fogarty et al. |
| 5,902,316 A | | 5/1999 | Mollenauer |
| 5,916,233 A | | 6/1999 | Chin |
| 5,922,004 A | | 7/1999 | DuBois |

(List continued on next page.)

FOREIGN PATENT DOCUMENTS

| | | |
|---|---|---|
| EP | 0 979 635 A2 | 2/2000 |
| WO | WO 99/66842 | 12/1999 |
| WO | WO 00/15116 | 3/2000 |

*Primary Examiner*—Roy D. Gibson
*Assistant Examiner*—Pete Vrettakos

(57) ABSTRACT

A surgical device for applying radio frequency energy to a portion of a captured vessel is provided. The device including: a first tube having an internal lumen for passage of a viewing device therein, the first tube having a substantially transparent first window at a distal tip thereof; a second tube slidingly disposed over the first tube, the second tube having a substantially transparent second window at a distal tip thereof, the second tube further having a slot for capturing a portion of the vessel; an actuator for sliding the second tube relative to the first tube between open and closed positions, wherein in the closed position an inner surface of the second window is aligned with an outer surface of the first window and captures the portion of the vessel therebetween; and at least one electrode affixed to one of the inner or outer surfaces and facing the other of the inner or outer surfaces for applying radio frequency energy to the captured portion of the vessel.

10 Claims, 4 Drawing Sheets

U.S. PATENT DOCUMENTS

| | | | |
|---|---|---|---|
| 5,928,135 A | 7/1999 | Knight et al. | |
| 5,938,680 A | 8/1999 | Ginn | |
| 5,968,065 A | 10/1999 | Chin | |
| 5,968,066 A | 10/1999 | Fogarty et al. | |
| 5,970,982 A | 10/1999 | Perkins | |
| 5,972,010 A | 10/1999 | Taheri | |
| 5,976,168 A | 11/1999 | Chin | |
| 5,980,549 A | 11/1999 | Chin | |
| 5,984,937 A | 11/1999 | Morse et al. | |
| 6,019,771 A | 2/2000 | Bennett et al. | |
| 6,022,313 A | 2/2000 | Ginn et al. | |
| 6,033,404 A * | 3/2000 | Melzer et al. | 606/46 |
| 6,036,713 A | 3/2000 | Kieturakis | |
| 6,036,714 A | 3/2000 | Chin | |
| 6,042,538 A | 3/2000 | Puskas | |
| 6,059,802 A | 5/2000 | Ginn | |
| 6,068,639 A | 5/2000 | Fogarty et al. | |
| 6,071,232 A | 6/2000 | Knighton et al. | |
| 6,120,434 A | 9/2000 | Kimura et al. | |
| 6,139,489 A | 10/2000 | Wampler et al. | |
| 6,190,384 B1 * | 2/2001 | Ouchi | 606/47 |
| 6,224,593 B1 * | 5/2001 | Ryan et al. | 606/41 |
| 6,267,761 B1 * | 7/2001 | Ryan | 606/50 |
| 6,572,615 B2 * | 6/2003 | Schulze et al. | 606/50 |

* cited by examiner

SURGICAL DEVICE FOR APPLYING RADIO FREQUENCY ENERGY TO A PORTION OF A CAPTURED VESSEL

CROSS REFERENCE TO RELATED APPLICATIONS

This application is a divisional of U.S. patent application Ser. No. 09/966,790, filed on Sep. 28, 2001 now U.S. Pat. No. 6,572,615.

BACKGROUND OF THE INVENTION

1. Field of the Invention

The present invention relates generally to surgical devices, and more particularly, to a surgical device for applying radio frequency energy to a portion of a captured vessel, preferably to a side branch of a vessel to be harvested for a coronary bypass graft (CABG).

2. Prior Art

Surgeons and surgical assistants have been using medical devices incorporating radio frequency (RF) electricity for many years to cauterize and coagulate bodily tissues during surgical procedures. Two types of RF surgical devices are conventionally utilized: mono-polar and bipolar. Both incorporate a pair of conductors for transmission of alternating RF electricity. In a mono-polar electrosurgical instrument, a first conducting electrode having a first polarity is typically placed on the patient's skin and communicates through the body, i.e. forms a conductive path, with a second conducting electrode having the opposite polarity located on the surgical instrument.

A bipolar electrosurgical instrument, however, typically incorporates both first and second electrodes of opposite polarity in the same surgical instrument, substantially restricting the flow path of electric current to tissue that is contained between the electrodes. As mentioned previously, both mono-polar and bipolar electrosurgical instruments apply RF energy through tissue. The energy is dissipated within the tissue in the form of heat due to the natural impedance of tissue. As the temperature of the tissue rises, the electrical resistivity of the tissue increases. When RF energy is applied to tissue, and as the temperature reaches about 67–70 degrees Celsius., the tissue begins to coagulate. As increasing amounts of energy dissipate in the tissue, the collagen forming the tissue matrix breaks down and appears to "melt". Mechanical compression of the coagulating tissue layers fuses and seals any contained blood vessels, so that the tissue may be cut without bleeding. When the tissue temperature reaches 100 degrees C., most fluids (including water) vaporize into the surrounding tissues and air.

The energy dissipation rate in tissue depends on numerous factors, including the inherent electrical resistivity of the tissue and the electrical current density. Electrical current density in various tissues is an important consideration in the design of the electrodes in a bipolar electrosurgical instrument, including the number, size, shape, and placement of the electrodes.

Many surgeons prefer to use bipolar electrosurgical instruments for hemostatically (without bleeding) sealing tissue prior to transection. Bipolar electrosurgical devices are known for grasping, coagulating, and cutting tissue. Typically the instruments have grasping elements, and one of the grasping elements is an electrically opposite pole of the other grasping element. For this type of conventional, bipolar electrical configuration, electrical current can be simplistically thought of as "flowing" from one grasping element (a positive pole), through the grasped tissue, and to the other grasping element (a negative pole).

In a coronary artery bypass graft (CABG) procedure, a surgeon or surgical assistant may remove a saphenous vein from one of the patient's legs to use as one or more bypass grafts on that patient's heart. In recent years, new surgical dissecting/retracting tools have been introduced to enable the surgical operator to harvest the saphenous vein endoscopically. Examples of endoscopic vessel harvesting devices and methods are contained in the following U.S. patents, which are incorporated by reference: U.S. Pat. Nos. 5,667,480; 5,722,934; 5,928,135; and 5,928,138. In such surgical procedures the operator "tunnels" with the surgical dissecting/retracting tool alongside the vein under the skin, working through a small incision made into the inside of the patient's leg or knee. The benefits of this procedure to the patient are numerous because endoscopic vein harvesting (EVH) results in greatly reduced recovery time and pain for the patient as compared to the earlier open procedure of creating an incision along the leg equal to the length of the vein harvested. In addition scarring is limited, and the incidence of serious infections reduced.

In conventional EVH procedures, the surgical operator uses the surgical dissecting/retracting tool to create a small working space at the distal end of the tool and adjacent to the vein being harvested. The tool generally has a lumen for insertion of an endoscope so that the procedure is performed under direct observation. As the operator maneuvers the tool along the vein to separate the vein from adjacent tissues, the operator typically encounters numerous smaller collateral vascular side branches of the main vein (usually about 15). To harvest the main vein with minimal bleeding of surrounding tissues, the operator may apply at least two conventional surgical clips to each side branch encountered, using a conventional mechanical endoscopic surgical clip applier. Then the clip applier is removed, an endoscopic scissors is inserted to cut the side branch between the applied clips. Each instrument insertion and removal is not only time-consuming, but care must be taken not to cause trauma to the vein being harvested and to surrounding tissues in the leg. The operator may also use bipolar electrosurgical scissors in place of mechanical clip appliers, which are well known in the art for use in this type of surgical procedure.

Therefore, surgeons must exchange instruments for ligating and transecting the side branches and must also coordinate the viewing of the image of the side branch with the manipulation of the ligation and transection instruments in order to ligate and transect the side branch.

SUMMARY OF THE INVENTION

Therefore it is an object of the present invention to provide a surgical device for applying radio frequency energy to a portion of a captured vessel to seal vessels under direct observation.

It is another object of the present invention to provide a surgical device for applying radio frequency energy to a portion of a captured vessel, which minimizes instrument exchanges.

Accordingly, a surgical device for applying radio frequency energy to a portion of a captured vessel is provided. The device comprises: a first tube having an internal lumen for passage of a viewing device therein, the first tube having a substantially transparent first window at a distal tip thereof; a second tube slidingly disposed over the first tube, the second tube having a substantially transparent second window at a distal tip thereof, the second tube further having a slot for capturing a portion of the vessel; actuation means for sliding the second tube relative to the first tube between open and closed positions, wherein in the closed position an inner surface of the second window is aligned with an outer surface of the first window and captures the portion of the vessel therebetween; and at least one electrode affixed to one of the inner or outer surfaces and facing the other of the inner or outer surfaces for applying radio frequency energy to the captured portion of the vessel. The first and second windows are preferably offset at an angle relative to an axial direction of the lumen and the slot is preferably flush and parallel with the inner surface of the second window. The captured vessel is preferably a side branch of an artery being harvested.

Preferably, the first tube comprises a proximal portion and a distal portion, wherein the distal portion including the first window is substantially transparent. More preferably, the device further comprises orientation means for maintaining the orientation of the first tube relative to the second tube such that the inner surface of the second window is aligned with the outer surface of the first window. The orientation means preferably comprises a slot on one of the first or second tubes and a corresponding key on the other of the first or second tubes such that the key is disposed in the slot to prevent relative rotation between the first and second tubes.

The actuation means preferably comprises at least one projection disposed on a proximal end of the second tube, wherein pulling the projection in a proximal direction slides the second tube relative to the first tube into the closed position and pushing the projection in a distal direction slides the second tube relative to the first tube into the open position.

The at least one electrode preferably comprises two electrodes affixed to the outer surface of the first window, each of the electrodes being of a different polarity. More preferably, the at least one electrode comprises at least two sets of electrodes affixed to the outer surface of the first window, each of the sets of electrodes having an electrode of a first polarity and an electrode of a second polarity, wherein the first and second polarities are opposite. The first window preferably further having holes, for connecting at least two electrodes of the same polarity through the holes and along an inner surface of the first window.

The device preferably further comprises flushing means for flushing at least one of the outer surface of the first window or inner surface of the second window with a liquid. The flushing means preferably comprises a conduit having a proximal end connected to a liquid source and a distal end adjacent to the first window, the distal end being configured to direct the liquid across at least one of the outer surface of the first window or the inner surface of the second window. The conduit is preferably disposed in an annular space between the first and second tubes and further comprising a spacer disposed in the annular space for maintaining a parallel relationship between the first and second tubes.

Also provided is a method for applying radio frequency energy to a portion of a captured vessel, the method comprising: providing a first tube having an internal lumen for passage of a viewing device therein, the first tube having a substantially transparent first window at a distal tip thereof and providing a second tube slidingly disposed over the first tube, the second tube having a substantially transparent second window at a distal tip thereof, the second tube further having a slot for capturing a portion of a vessel, at least one electrode being affixed to one of the inner or outer surfaces and facing the other of the inner or outer surfaces; viewing the vessel through the first and second windows; capturing a portion of the vessel in the slot; sliding the second tube relative to the first tube between open and closed positions, wherein in the closed position an inner surface of the second window is aligned with an outer surface of the first window to sandwich the portion of vessel therebetween; and applying radio frequency energy to the at least one electrode to cauterize the captured portion of vessel.

Preferably the method further comprises maintaining the orientation of the first tube relative to the second tube such that the inner surface of the second window is aligned with the outer surface of the first window.

The sliding step preferably comprises fixing the first tube relative to the endoscope and pulling a projection disposed on the second tube in a proximal direction to slide the second tube relative to the first tube into the closed position and pushing the projection in a distal direction to slide the second tube relative to the first tube into the open position. The method preferably further comprises flushing at least one of the outer surface of the first window or inner surface of the second window with liquid.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE PREFERRED EMBODIMENT

Although this invention is applicable to numerous and various types of vessels, it has been found particularly useful in the environment of CABG to apply RF energy to a side branch of an artery to be harvested. Therefore, without limiting the applicability of the invention to the environment to CABG and the application of RF energy to a side branch of an artery to be harvested, the invention will be described in such environment.

Figure 1:
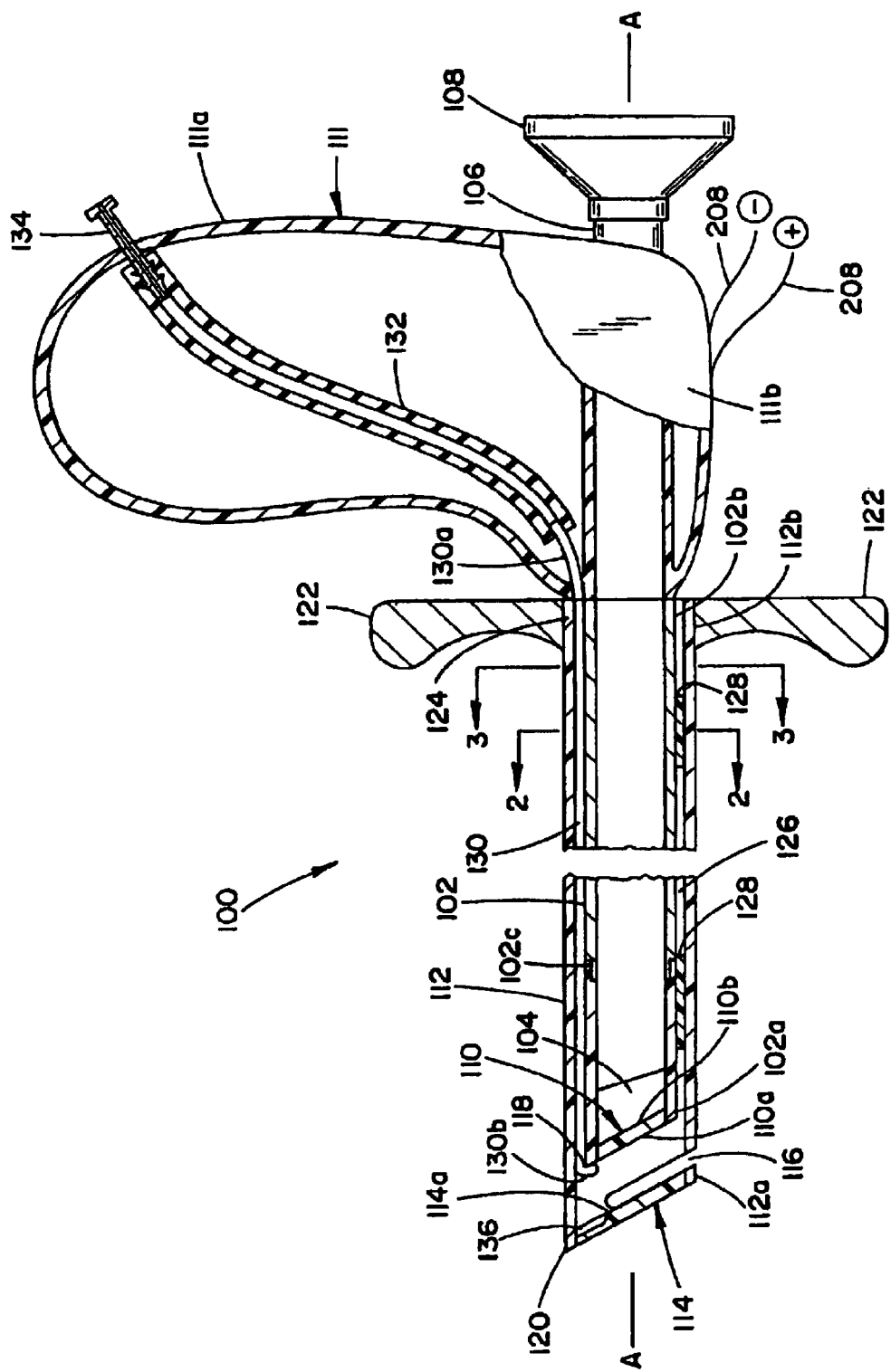
FIG. 1 illustrates a cross sectional side view of a preferred implementation of the surgical device of the present invention.

Referring now to FIG. 1, a surgical device for applying radio frequency energy to a portion of a captured vessel is illustrated therein, the surgical device generally being referred to by reference numeral 100. The surgical device comprises a first tube 102 having an internal lumen 104 along a central axis A for passage of a viewing device therein, such as an endoscope 106. The endoscope 106 can have an eyepiece 108 to provide an optical view, as illustrated, or can provide a digital image on a display monitor (not shown). The first tube 102 has a substantially transparent first window 110 at a distal tip 102a. The first tube either slides over the endoscope 106 to abut the handle 111, slides over a sleeve (not shown) fixed to the handle 111, or is itself fixed to the handle 111. The first tube 102 is preferably fabricated from a medical grade metal such as stainless steel, while the first window 110 is preferably fabricated from a medical grade glass or a medical grade clear polymer, such as polycarbonate. The length of the first tube 102 is determined by the length of the endoscope 106 inserted therein. The first window is affixed to the distal end 102a of the first tube 102 by any means known in the art, such as by means of a press fit or with a medical grade epoxy. More preferably, the first tube comprises a metal proximal portion 102b and a transparent distal tip 102a portion, including the first window 110. The distal and proximal portions are connected at a joint 102c, which is preferably either a press fit or an epoxied joint using any suitable grade medical epoxy. Although the first window 110 can be oriented perpendicular to the central axis A, it is preferred that it is angled with respect to the central axis A, preferably at an angle of approximately 45 degrees.

The surgical device 100 also includes a second tube 112 slidingly disposed over the first tube 102. More preferably, the entire second tube 112 is fabricated of the substantially transparent material. Alternatively, the second tube 112 can have a construction similar to the two piece preferred construction of the first tube 102 described above. The second tube 112 also has a substantially transparent second window 114 at a distal tip 112a thereof. Like the First window, 110, the second window 114 is preferably a medical grade glass or a clear plastic, such as polycarbonate. The second window is preferably offset from the central axis A by the same degree as the first window 110 such that the first and second windows 110, 114, respectively, move in a parallel relationship.

The second tube 114 further has a slot 116, which as will be described below, is for capturing a portion of a vessel therein. The slot 116 is preferably sized to accommodate common sizes of side branches encountered when harvesting a vein for use in a CABG procedure. The slot 116 is also preferably oriented parallel to the first and second windows 110, 114, respectively, as illustrated in FIG. 1. The edges of the slot 116 are preferably rounded to avoid tearing of any encountered vessels, as are the edges 118, 120 of the first and second tubes 102, 112, respectively.

Figure 6:
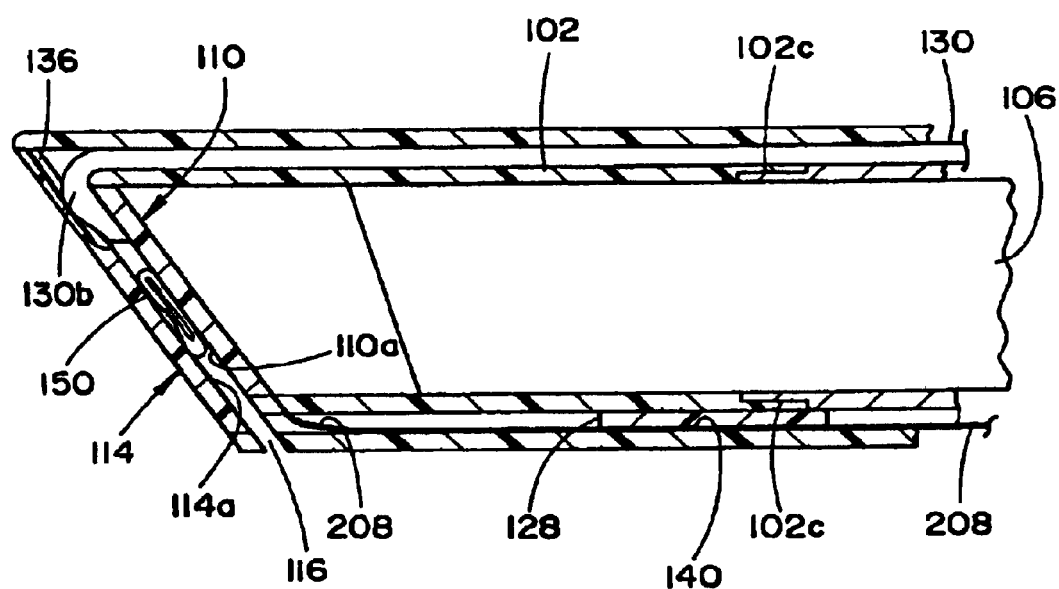
FIG. 6 illustrates an enlarged distal portion of the surgical device of FIG. 1 where a vessel is captured in the slot of the second tube.

An actuation means is provided for sliding the second tube 112 relative to the first tube 114 between an open position (shown in FIG. 1) and a closed position (shown in FIG. 6). In the closed position, an inner surface 114a of the second window 114 is aligned with an outer surface 110a of the first window 110. The actuation means preferably comprises at least one projection 122 disposed on a proximal end 112b of the second tube 112. Preferably, the actuation means comprises two projections 122 which can be manipulated by the fingers of the surgeon to either pull the second tube 112 proximally relative to the first tube 102 into the closed position or to push the second tube 112 distally relative to the first tube 102 into the open position. The second tube 112 can be biased with a biasing means, such as a spring (not shown), into either one of the closed or open positions. The projections 122 are preferably of a unitary construction and include an opening 124 cooperating with the proximal end 112b of the second tube 112. The projections 122 can be affixed to the proximal end 112b of the second tube 112 by any means known in the arts, such as by a press fit or with a medical grade epoxy.

Figure 4:
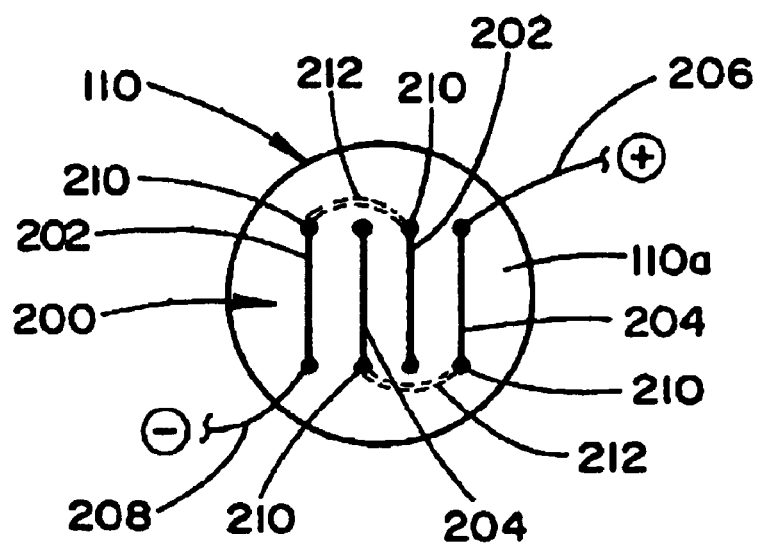
FIG. 4 illustrates the outer surface of a first window having bipolar electrodes affixed thereon.

Referring now to FIG. 4, the surgical device 100 further has at least one electrode 200 affixed to the inner surface 114a of the second window 114 or to the outer surface 110a of the first window 110 and facing the other of the inner or outer surfaces 114a, 110a, respectively. Preferably, the at least one electrode 200 comprises two electrodes 202, 204 affixed to the outer surface 110a of the first window 110 where each of the electrodes 202, 204 are of a different polarity. RF energy is preferably supplied by an electrosurgical generator (not shown) via wires 206, 208 which are preferably routed from the handle 111 to the first window 110, as will be discussed below. Thus, a vessel captured in the slot 116 is squeezed between the inner surface 114a of the second window 114 and the outer surface 110a of the first window 110 to provide an electrical path from one electrode 202 to another 204.

Preferably, at least two sets of electrodes 200 are provided as shown in FIG. 4. The electrodes are preferably applied to the outer surface 110a of the first window 110 by metal deposition, which is well known in the art. The wires 206, 208 are preferably connected to the electrodes 200 by soldering, as is also well known in the art. The different sets of electrodes 200 are preferably arranged such that their polarities alternate as shown in FIG. 4. Preferably, to arrange the electrodes 200 in the alternating fashion, holes 210 are provided. The holes 210 are filled with conductive material and leads 212 are formed on the inner surface 110b of the first window 110 to connect the electrodes 200 of the same polarity. The leads 212 and the filling of the holes 210 are preferably made by metal deposition methods known in the art.

The bipolar arrangement of electrodes is shown and described by way of example only and not to limit the scope and spirit of the present invention. Other electrode arrangements are possible, such as a monopolar electrode arrangement where at least one monopolar electrode is disposed on the outer surface 110a of the first window 110 and a ground plate is used therewith, as is known in the art.

Figure 2:
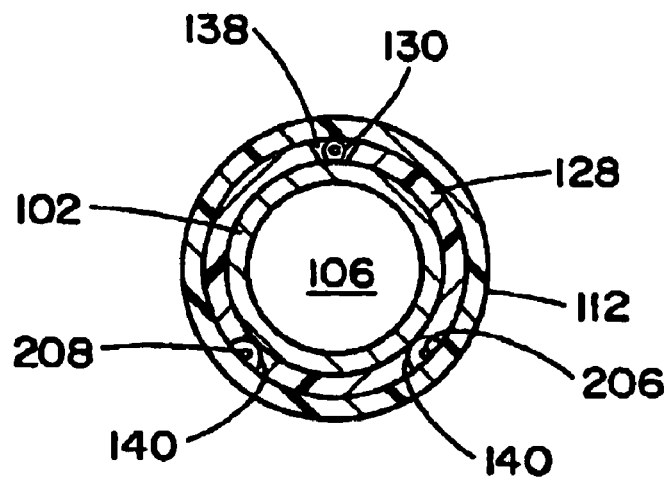
FIG. 2 illustrates a cross sectional view of the surgical device of FIG. 1 taken along line 2—2.

Referring now to FIGS. 1 and 2, the second tube 112 can slidingly engage the first tube 102 without any, or any appreciable, annular space therebetween. However, it is preferred that an annular space 126 is formed between the first and second tubes 102, 112, for the routing of additional components of the device 100. The annular space 126 preferably has at least one, and more preferably, two spacers 128 fabricated of a resilient medical grade material and preferably having a low coefficient of friction, such as Teflon. Preferably, a flushing means is provided in the annular space 126 for flushing at least one of the outer surface 110a of the first window 110 or inner surface 114a of the second window 114 with a liquid, such as saline, to remove any debris from the same. Preferably, the flushing means comprises a flushing tube 130 (not shown sectioned in FIG. 1 for clarity) disposed in the annular space 128 and running longitudinally along the first tube 102. The flushing tube 130 preferably is connected at a proximal end 130a to flexible tubing 132 disposed in the handle 111. The flexible tubing 132 in turn is preferably connected to a luer fitting 134 disposed on the handle 111. The handle is preferably of a clamshell design, which includes two halves 111a, 111b, which are fit together, allowing assembly of the internal flexible tubing 132 therein. Alternatively, the internal tubing 132 can be replaced with a molded conduit formed when the two handle halves are placed together.

The luer fitting 134 is connected to a pressurized source of fluid, such as saline. The fluid source is preferably a syringe, pump, or water bottle, as is known in the art. A distal end 130b of the flushing tube 130 is preferably shaped to disperse the fluid over the outer surface 110a of the first window 110 or the window having the electrodes 200. In order to accommodate the distal end 130b of the flushing tube 130, a cavity 136 is provided on the inner surface 114a of the second window 114 such that the distal end 130b does not interfere with the sliding of the second window 114 to meet or substantially meet the first window 110. Also provided to accommodate the flushing tube 130 are slots 138 in each of the spacers 128.

Referring now to FIGS. 1, 2, and 6, also provided in the annular space 128 are wires 206, 208 which preferably are run longitudinally in the annular space 128 from the handle 111 to the electrodes 200. To accommodate the wires 206, 208 in the annular space 128, grooves 140 are provided on the spacers 128.

Figure 3:
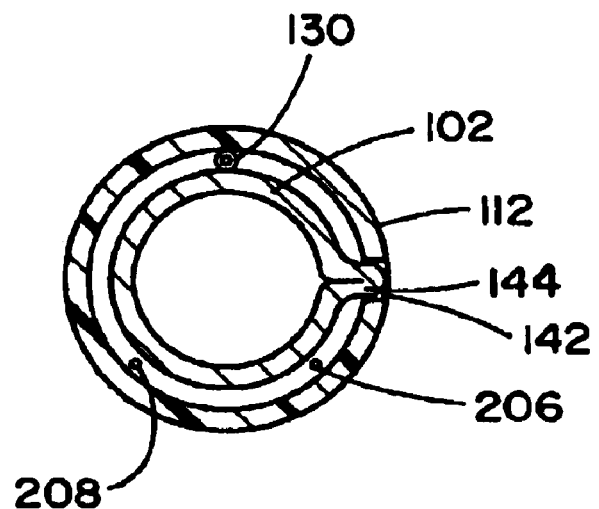
FIG. 3 illustrates a cross sectional view of the surgical device of FIG. 1 taken along line 3—3.

Referring now to FIGS. 1 and 3, the device 100 preferably also has an orientation means for maintaining the orientation of the first tube 102 relative to the second tube 112 such that the inner surface 114a of the second window 114 is aligned with the outer surface 110a of the first window 110 (i.e., the first and second windows 114, 110 are maintained in a parallel relationship). The orientation means preferably comprises a slot 142 on either the first tube 102 or the second tube 112 and a corresponding key 144 on the other of the first tube 102 or second tube 112 such that the key 144 is slidingly disposed in the slot 142 to prevent relative rotation between the first and second tubes 102, 112 yet allow sliding motion between the same. The slot 142 is preferably formed in the second tube 112 by any conventional machining or punching methods known in the art. The key 144 is preferably formed on the first tube 102, preferably by crimping a portion of the first tube's wall. However, other methods can also be used to form the key 144, such as by welding a protrusion on the wall of the first tube 102.

Figure 5:
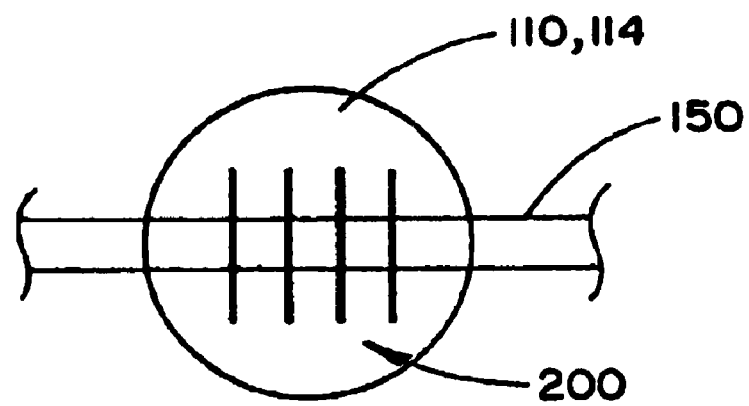
FIG. 5 illustrates a view of the first window from an endoscope where a vessel is captured in the slot of the second tube.

The operation of the preferred surgical device 100 will now be described with reference to FIGS. 1, 5, and 6. As discussed above, the surgical device 100 of the present invention applies radio frequency energy to a portion of a captured vessel 150, preferably to a side branch of a vessel being harvested for a CAGB procedure. While dissecting an artery to be harvested, or otherwise encountering a vessel 150 to be ligated and transected, the vessel is viewed through the first and second windows 110, 114 as illustrated in FIG. 5. The device 100 may be used for the dissection (tunneling) while endoscopically visualizing tissue structures impinging on the distal tip, or outer surface of the second window 114. The 45 degree offset of the windows 110, 114 facilitate the dissection of tissue by helping the device slide through tissue layers with minimal pushing force by the operator. While viewing the vessel 150 by means of the viewing device 106, the electrodes 200 are superimposed over the image of the vessel 150 as is also illustrated in FIG. 5. While the surgical device 100 is in the open position as illustrated in FIG. 1, the surgical device 100 is manipulated with the handle 111 to capture a portion of the vessel 150 in the slot 116.

Once the portion of vessel 150 is captured in the slot 116, the second tube 112 is slid relative to the first tube 102 from the open position to the closed position shown in FIG. 6. In the closed position, an inner surface 114a of the second window 114 is aligned with an outer surface 110a of the first window 110 to sandwich the portion of vessel 150 therebetween. The portion of the vessel 150 captured in the slot 150 is then between the first and second windows 110, 114 similar to how a specimen is sandwiched between glass plates when being viewed with a microscope. While the portion of vessel 150 is captured and sandwiched between the first and second windows 110, 114, the electrodes 202, 204 are in contact with the vessel 150 and the vessel completes a circuit between the electrodes 202, 204 of different polarity. The portion of vessel 150 is then cauterized to ligate the same by applying radio frequency energy from the electrosurgical generator (not shown) to the electrodes 200. The RF energy is applied by the activation of a switch (not shown), which can be provided on the handle 111 or as a foot switch as is known in the art.

The first and second windows 110, 114 are preferably flat, to not only provide a uniform compression of tissue captured therebetween, but to provide optical clarity of tissue structures viewed through the windows 110, 114. The ability of the operator to clearly view the tissue structures, including vessels through the windows 110, 114, eliminates the need for a separate optical dissecting tool for loosening tissue around a vessel. Thus, those skilled in the art will appreciate that the device 100 of the present invention provides a viewing means, a dissection means, a ligating means, and a transection means all in a single instrument.

After ligating the portion of captured vessel 150, debris from the cauterization, other debris, or bodily fluids such as bile or blood can accumulate on the first or second window 110, 114, most likely on the window with the electrodes 200. Therefore, subsequent to the ligation, at least the first window 110 is flushed with liquid, preferably with saline. Preferably, the outer surface 110a of the first window 110 is flushed with the flushing means discussed above by connecting the luer fitting 134 to a water bottle, syringe, or pump to supply the liquid under pressure to the outer surface 100a of the first window 110. However, the device 100 can also be removed from the body and the windows 110, 114 manually washed as is known in the art, such as by dipping the distal end of the device 100 in a saline washbowl.

Also subsequent to the ligation of the portion of vessel 150, the ligated portion is preferably severed to cut the vessel. The cutting of the ligated vessel can be done using a separate cutting instrument, while under observation of the endoscope 106. Alternatively, the ligated vessel can be cut with a cutting means (not shown) provided integral with the surgical device 100 of the present invention.

EXAMPLE

As discussed above, the present invention has particular utility in a coronary artery bypass graft procedure (CABG), however, the use of the instruments of the present invention is now described with regard to the CABG procedure by way of example only and not to limit the scope or spirit of the present invention. A patient is prepared for cardiac surgery in a conventional manner using conventional techniques and procedures. The patient is then anesthetized and ventilated using conventional techniques. A conventional CABG procedure is performed by harvesting the greater saphenous vein from one or both of the patient's legs. The surgeon prepares an opening to the heart by dividing the patient's sternum (conventional median sternotomy) and spreading the rib cage apart using a surgical retractor. The surgeon next begins dissecting the internal mammary artery (IMA) from the chest wall of the patient, so that the distal end of the vessel may be anastomosed to the diseased lower anterior descending (LAD) coronary artery on the distal side of a lesion on the septum near the left ventricle of the heart as a source of oxygenated blood. During the surgical procedure, the surgeon optionally elects to have the patient's heart beating to perform a conventional beating heart CABG, although the surgeon has a cardiopulmonary bypass machine (CPB) primed with the patient's blood and available if it is necessary to convert the beating heart procedure into a conventional stopped heart procedure.

The surgeon prepares the heart for attaching the graft vessels by cutting and pulling away the pericardium. After checking the graft vessels for patency, collateral damage and viability, the surgeon prepares to do the anastomoses necessary to bypass the lesions in the coronary arteries. The surgeon sutures the proximal end of each graft vessel to the patient's aorta and the distal end to the diseased coronary artery, distal to the blockage or lesion. The distal end of the LAD is similarly anatomosed to a coronary artery distal to a lesion in a conventional manner. The surgeon checks the bypass grafts for adequate blood flow in a conventional manner, and then completes the remainder of the operation in a conventional manner.

The veins used in the CABG procedure are harvested endoscopically using the surgical instruments of the present invention. Using these instruments, initially the patient's leg is positioned to be slightly bent and is turned to expose the inner leg. A marker is used to show on the skin the location of the vein to be harvested. Then an incision is created on the inner leg near the knee, through the skin and subcutaneous layers. The vein typically lies directly beneath the subcutaneous layers and so a middle portion of the vein is accessed through the incision. After some initial dissection with conventional blunt dissectors around this portion of the vein, a surgical instrument is introduced into the incision. An endoscope provides visualization of the vein and surrounding tissue within the working space inside the head. The instrument is advanced along the vein. Side branches off of the vein are ligated and divided a few millimeters away from the vein, taking great care not to injure the vein in any way. The harvesting procedure continues in this manner until the vein is hemostatically isolated from surrounding tissues and blood supply along the portion to be harvested. Then stab incisions are created through the skin and subcutaneous layers at the distal and proximal ends of the vein, ligation clips are applied, and the vessel is transected in order to remove the vein from the knee incision. Thee harvested vein is prepared for use as grafts in a conventional manner.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A method for applying radio frequency energy to a portion of a captured vessel, the method comprising:
    providing a first tube having an internal lumen for passage of a viewing device therein, the first tube having a substantially transparent first window at a distal tip thereof and providing a second tube slidingly disposed over the first tube, the second tube having a substantially transparent second window at a distal tip thereof, the second tube further having a slot for capturing a portion of a vessel, at least one electrode being affixed to one of the inner or outer surfaces and facing the other of the inner or outer surfaces;
    viewing the vessel through the first and second windows;
    capturing a portion of the vessel in the slot;
    sliding the second tube relative to the first tube between open and closed positions, wherein in the closed position an inner surface of the second window is aligned with an outer surface of the first window to sandwich the portion of vessel therebetween; and
    applying radio frequency energy to the at leant one electrode to cauterize the captured portion of vessel.

2. The method of claim 1, further comprising maintaining the of the first tube relative to the second tube such that inner surface of the second window is aligned with the outer surface of the first window.

3. The method of claim 1, wherein the sliding step comprises fixing the first tube relative to the endoscope and pulling a projection disposed on the second tube in a proximal direction to slide the second tube relative to the first tube into the closed position and pushing the projection in a distal direction to elide the second tube relative to the first tube into the open position.

4. The method of claim 1, further comprising flushing at least one of the outer surface of the first window or inner surface of the second window with liquid.

5. The method of claim 1, wherein the captured vessel is a side branch of an artery being harvested.

6. A method for applying a cauterization energy to a portion of a captured vessel, the method comprising:
    observing the vessel between tint and second transparent members;
    capturing the portion of the vessel between the first and second transparent members; and
    applying the cauterization energy to at least one of the first and second transparent members to cauterize the captured portion of vessel.

7. The method of claim 6, wherein the first and second transparent members are disposed on first and second tubes, respectively, and wherein the moving step comprises sliding one of the first and second tubes relative to the other of the first and second tubes into a closed position to capture the portion of the vessel.

8. The method of claim 6, further comprising flushing at least one of an outer surface of the first transparent member or an inner surface of the second transparent member with liquid.

9. The method of claim 6, wherein at least one of the first and second transparent members has an electrode disposed thereon, and wherein the applying comprises energizing the electrode with radio frequency energy.

10. The method of claim 6, wherein captured vessel is a side branch of an artery being harvested.

* * * * *

UNITED STATES PATENT AND TRADEMARK OFFICE
CERTIFICATE OF CORRECTION

PATENT NO. : 6,835,195 B2
DATED : December 28, 2004
INVENTOR(S) : Schulze et al.

It is certified that error appears in the above-identified patent and that said Letters Patent is hereby corrected as shown below:

Column 10,
Line 15, between "the" and "of the first tube" insert the word -- orientation --.
Line 24, please delete "elide" and insert -- slide --.

Signed and Sealed this

Twenty-fourth Day of May, 2005

JON W. DUDAS
*Director of the United States Patent and Trademark Office*